United States Patent
Snow

(10) Patent No.: US 11,191,938 B2
(45) Date of Patent: Dec. 7, 2021

(54) INTRODUCER SHEATH AND METHODS

(71) Applicant: Merit Medical Systems, Inc., South Jordan, UT (US)

(72) Inventor: Jeremy W. Snow, South Jordan, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 335 days.

(21) Appl. No.: 14/600,660

(22) Filed: Jan. 20, 2015

(65) Prior Publication Data

US 2015/0201963 A1    Jul. 23, 2015

Related U.S. Application Data

(60) Provisional application No. 61/929,614, filed on Jan. 21, 2014.

(51) Int. Cl.
  *A61B 10/02*      (2006.01)
  *A61B 17/34*      (2006.01)
  (Continued)

(52) U.S. Cl.
  CPC ......... *A61M 39/02* (2013.01); *A61B 10/0233* (2013.01); *A61B 17/3421* (2013.01);
  (Continued)

(58) Field of Classification Search
  CPC .. A61M 2039/0273; A61M 2039/0276; A61M 2039/0229; A61M 2039/0232; A61M 39/06; A61M 2039/062; A61M 2039/0633; A61M 2039/0027; A61M 25/0028; A61M 17/34; A61M 17/3498; A61M 17/3462
  See application file for complete search history.

(56) References Cited

U.S. PATENT DOCUMENTS 4,785,826 A    11/1988   Ward
4,922,602 A *   5/1990   Mehl .................... A61B 10/025
                                                      264/263
(Continued)

FOREIGN PATENT DOCUMENTS

AT        366546      6/1976
EP        0583144     2/1994
(Continued)

OTHER PUBLICATIONS

International Search Report and Written Opinion dated Apr. 30, 2015 for PCT/US2015/012002.
(Continued)

*Primary Examiner* — Bhisma Mehta
*Assistant Examiner* — William R Frehe
(74) *Attorney, Agent, or Firm* — Stoel Rives LLP

(57) ABSTRACT

A medical device for accessing body tissue or fluid is disclosed. The medical device may include an introducer sheath and a valve that impedes the flow of fluid through the introducer sheath. An assembly for selectively coupling components of a medical device is also disclosed. The assembly may comprise two components configured to engage with one another by at least a snap fit-type connection. This connection may facilitate disengagement of the two components via actuation of a release mechanism.

22 Claims, 9 Drawing Sheets

(51) Int. Cl.
*A61M 39/02* (2006.01)
*A61M 39/06* (2006.01)
*A61M 39/10* (2006.01)
*A61B 17/00* (2006.01)

(52) U.S. Cl.
CPC .......... *A61M 39/06* (2013.01); *A61B 17/3462* (2013.01); *A61B 17/3498* (2013.01); *A61B 2017/00477* (2013.01); *A61M 39/10* (2013.01); *A61M 2039/0202* (2013.01); *A61M 2039/062* (2013.01); *A61M 2039/0633* (2013.01); *A61M 2039/1027* (2013.01)

(56) References Cited

U.S. PATENT DOCUMENTS

| | | | |
|---|---|---|---|
| 5,172,702 A | | 12/1992 | Leigh et al. |
| 5,176,648 A | * | 1/1993 | Holmes ............... A61B 17/34 604/180 |
| 5,368,574 A | * | 11/1994 | Antonacci ......... A61M 25/0662 604/167.02 |
| 5,655,542 A | | 8/1997 | Weilandt |
| 5,788,651 A | | 8/1998 | Weilandt |
| 5,800,389 A | | 9/1998 | Burney et al. |
| 5,842,999 A | | 12/1998 | Pruitt et al. |
| D418,223 S | | 12/1999 | Phipps et al. |
| D428,150 S | | 7/2000 | Ruf et al. |
| 6,126,617 A | | 10/2000 | Weilandt et al. |
| 6,196,978 B1 | | 3/2001 | Weilandt et al. |
| 6,322,523 B2 | | 11/2001 | Weilandt et al. |
| D457,955 S | | 5/2002 | Bilitz |
| D463,555 S | | 9/2002 | Etter et al. |
| 6,488,662 B2 | | 12/2002 | Sirimanne |
| 6,497,687 B1 | | 12/2002 | Blanco |
| 6,656,195 B2 | | 12/2003 | Peters et al. |
| D490,152 S | | 5/2004 | Myall et al. |
| 7,041,065 B2 | | 5/2006 | Weilandt et al. |
| 7,247,160 B2 | | 7/2007 | Seiler et al. |
| D571,009 S | | 6/2008 | Smith et al. |
| 7,470,237 B2 | | 12/2008 | Beckman et al. |
| D586,916 S | | 2/2009 | Faulkner et al. |
| D598,543 S | | 8/2009 | Vogel et al. |
| 7,608,048 B2 | | 10/2009 | Goldenberg |
| D612,044 S | | 3/2010 | Scheibe |
| D612,051 S | | 3/2010 | Ruf |
| D619,251 S | | 7/2010 | Justiniano-Garcia et al. |
| D628,293 S | | 11/2010 | Ruf |
| 8,137,317 B2 | | 3/2012 | Osypka |
| 9,392,998 B2 | | 7/2016 | Snow |
| 2001/0009979 A1 | | 7/2001 | Weilandt et al. |
| 2003/0153842 A1 | | 8/2003 | Lamoureux et al. |
| 2004/0054377 A1 | | 3/2004 | Foster et al. |
| 2004/0215103 A1 | | 10/2004 | Meuller, Jr. et al. |
| 2005/0054947 A1 | | 3/2005 | Goldenberg |
| 2005/0125017 A1 | | 6/2005 | Kudrna et al. |
| 2006/0085019 A1 | | 4/2006 | Cote et al. |
| 2006/0211992 A1 | * | 9/2006 | Prosek ............... A61B 17/3421 604/167.06 |
| 2006/0224082 A1 | | 10/2006 | Vetter et al. |
| 2007/0027407 A1 | | 2/2007 | Miller |
| 2007/0078442 A1 | * | 4/2007 | Mayse ............... A61M 39/10 604/533 |
| 2007/0078472 A1 | | 4/2007 | Singh |
| 2007/0093778 A1 | * | 4/2007 | Cindrich ............... A61M 5/158 604/500 |
| 2007/0142744 A1 | | 6/2007 | Provencher |
| 2007/0179403 A1 | | 8/2007 | Heske et al. |
| 2007/0191775 A1 | * | 8/2007 | Diep ............... A61M 39/0606 604/164.01 |
| 2007/0250037 A1 | | 10/2007 | Brimhall et al. |
| 2008/0161720 A1 | | 7/2008 | Nicoson |
| 2008/0200833 A1 | | 8/2008 | Hardin et al. |
| 2008/0228104 A1 | | 9/2008 | Uber et al. |
| 2008/0281223 A1 | | 11/2008 | Goldenberg |
| 2008/0294145 A1 | * | 11/2008 | Eddings ............ A61M 25/0097 604/533 |
| 2008/0300507 A1 | | 12/2008 | Figueredo et al. |
| 2009/0275966 A1 | | 1/2009 | Mitusina |
| 2009/0143698 A1 | | 6/2009 | Janssens |
| 2009/0259200 A1 | | 10/2009 | Lampropoulos et al. |
| 2009/0299220 A1 | | 12/2009 | Field et al. |
| 2010/0010526 A1 | | 1/2010 | Mitusina |
| 2010/0130887 A1 | | 5/2010 | Selis |
| 2010/0168773 A1 | | 7/2010 | Funderburk et al. |
| 2010/0179484 A1 | * | 7/2010 | Carrez ................ A61M 39/045 604/187 |
| 2011/0251631 A1 | | 10/2011 | Trees et al. |
| 2012/0220894 A1 | | 8/2012 | Melsheimer |
| 2013/0131548 A1 | | 5/2013 | McGhit et al. |
| 2013/0150795 A1 | | 6/2013 | Snow |
| 2014/0100479 A1 | | 4/2014 | Tripp et al. |
| 2014/0171826 A1 | | 6/2014 | Lampropoulos et al. |
| 2014/0207021 A1 | | 7/2014 | Snow |
| 2014/0207069 A1 | * | 7/2014 | Bierman ........... A61M 25/0668 604/167.03 |
| 2014/0276453 A1 | * | 9/2014 | Woehr ............... A61M 25/0606 604/246 |
| 2015/0045828 A1 | | 2/2015 | Mcarthur et al. |
| 2015/0094751 A1 | | 4/2015 | Chen et al. |
| 2015/0201917 A1 | | 7/2015 | Snow |
| 2016/0089208 A1 | | 3/2016 | Vetter |

FOREIGN PATENT DOCUMENTS

| | | |
|---|---|---|
| EP | 0966920 | 12/1999 |
| EP | 1661521 | 5/2006 |
| WO | WO1996/22733 | 8/1996 |
| WO | WO1999/44505 | 9/1999 |
| WO | WO2006/013389 | 2/2006 |

OTHER PUBLICATIONS

International Search Report and Written Opinion dated Jan. 16, 2015 for PCT/US2015/011746.
International Search Report and Written Opinion dated Apr. 3, 2014 for PCT/US2013/076418.
International Search Report and Written Opinion dated Jun. 23, 2015 for PCT/US2013/076418.
International Preliminary Report dated Jul. 19, 2016 for PCT/US2015/011746.
Office Action dated Mar. 20, 2017 for U.S. Appl. No. 14/598,457.
U.S. Appl. No. 29/495,581, filed Jul. 2, 2014, Snow.
U.S. Appl. No. 14/598,457, filed Jun. 16, 2015, Snow.
Shuttle® and CT-Core® Semi-Automatic devices; Updated to the website between No. 8, 2012-Jan. 24, 2013. Accessed website on Jun. 27, 2014 at http://www.vigeohealthcare.com/gb/int_radiplogy.html.
International Search Report and Written Opinion dated May 1, 2014 for PCT/US2014/012043.
European Search Report dated Aug. 17, 2017 for EP15737182.4.
Office Action dated Aug. 28, 2017 for U.S. Appl. No. 14/598,457.
Office Action dated Jan. 25, 2018 for U.S. Appl. No. 14/598,457.
European Search Report dated Nov. 13, 2017 for EP15740963.2.
Office Action dated Mar. 26, 2018 for U.S. Appl. No. 15/184,551.
Office Action dated Sep. 4, 2018 for U.S. Appl. No. 14/598,457.
Office Action dated Oct. 9, 2018 for U.S. Appl. No. 15/184,551.
Office Action dated Feb. 26, 2019 for U.S. Appl. No. 15/184,551.
Office Action dated Mar. 1, 2019 for U.S. Appl. No. 14/598,457.
Notice of Allowance dated Oct. 23, 2019 for U.S. Appl. No. 15/184,551.
Notice of Allowance dated Nov. 27, 2019 for U.S. Appl. No. 14/598,457.
Office Action dated Aug. 9, 2019 for U.S. Appl. No. 14/598,457.

* cited by examiner

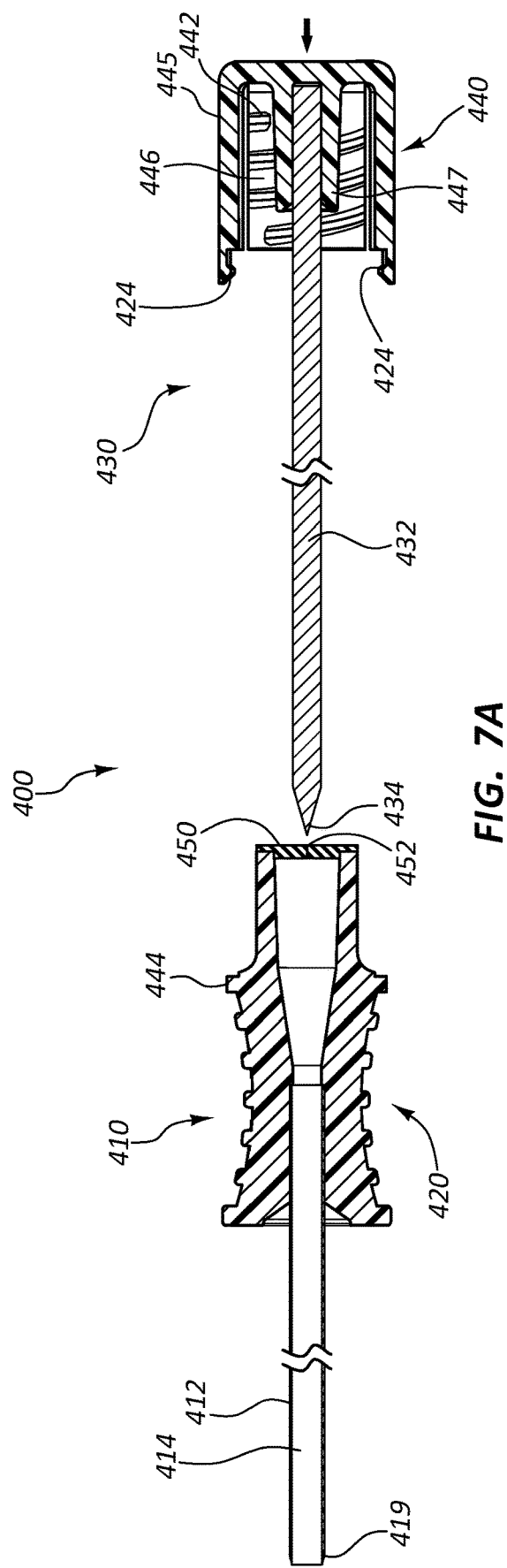
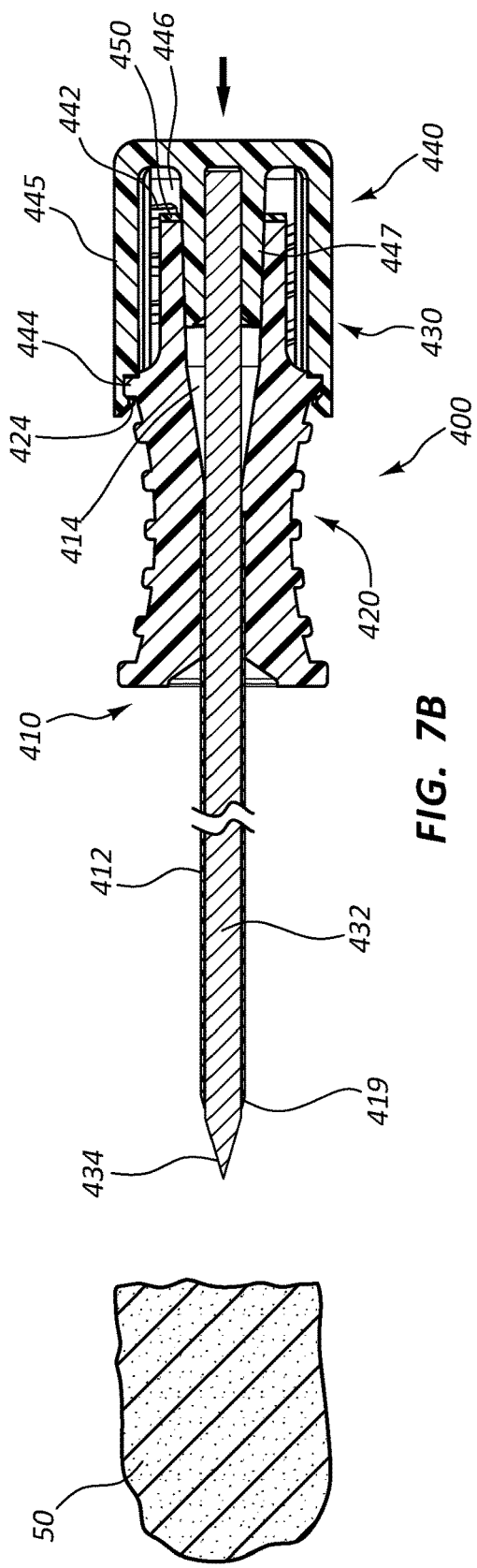
FIG. 7A
FIG. 7B

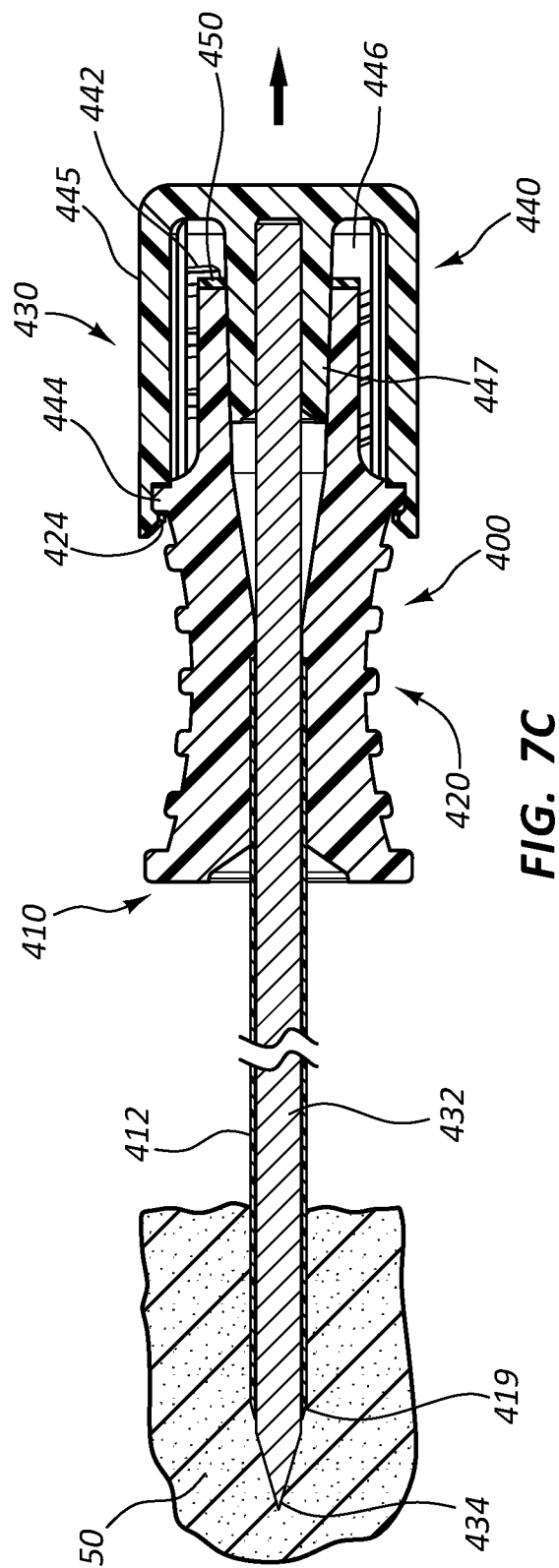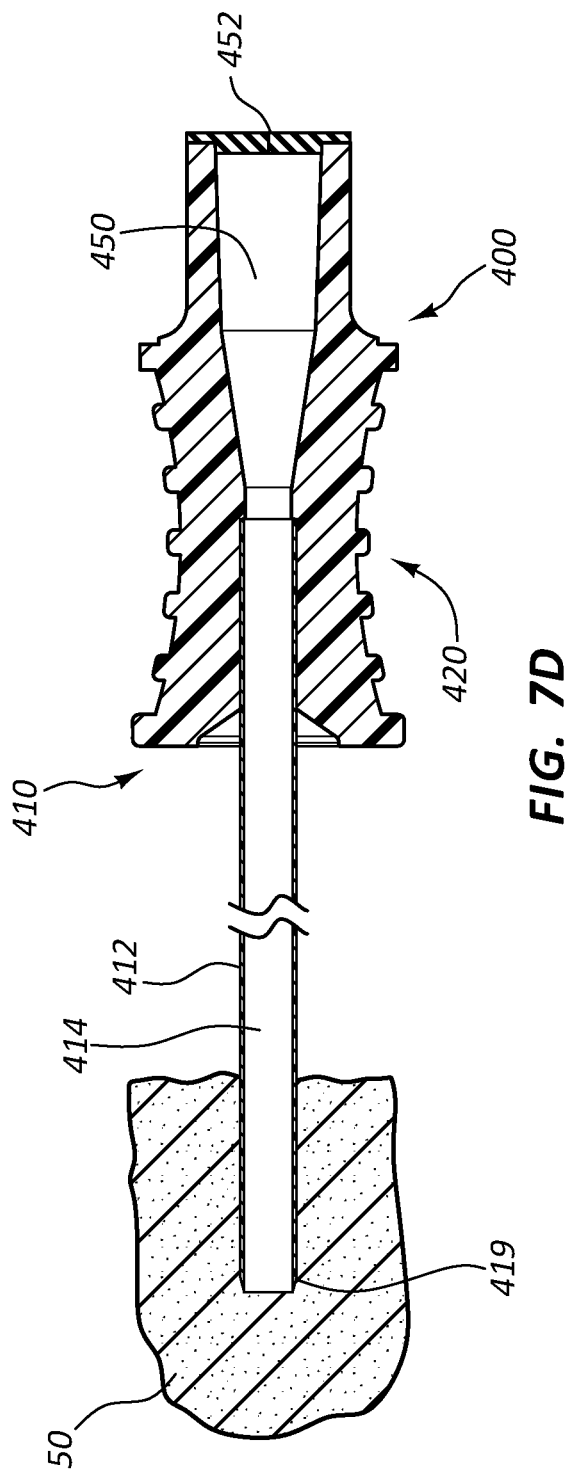

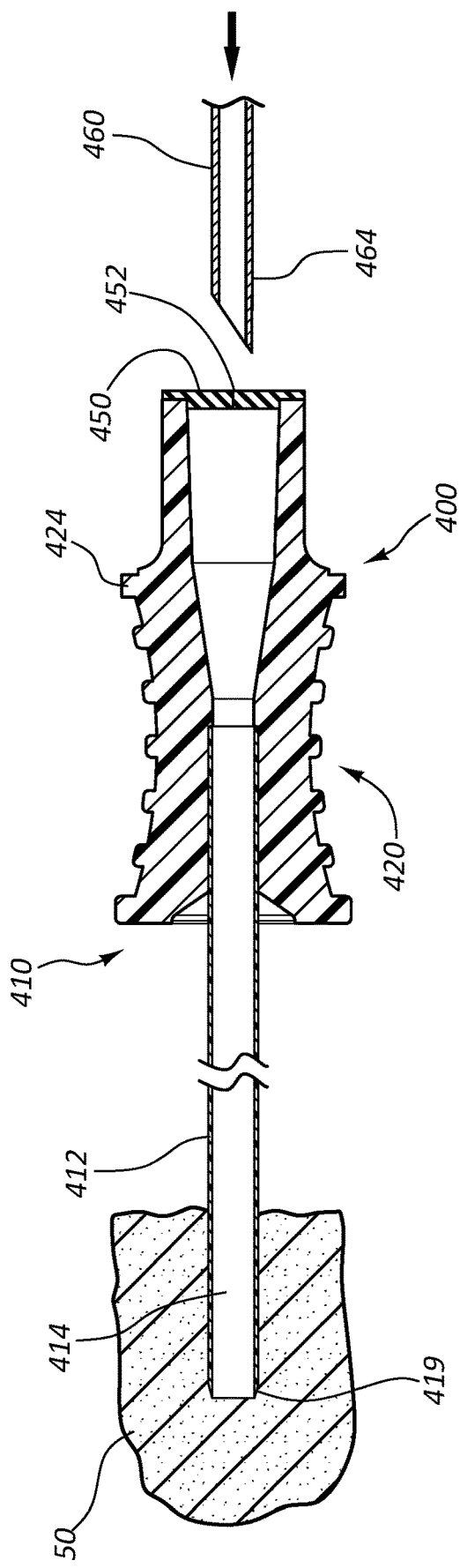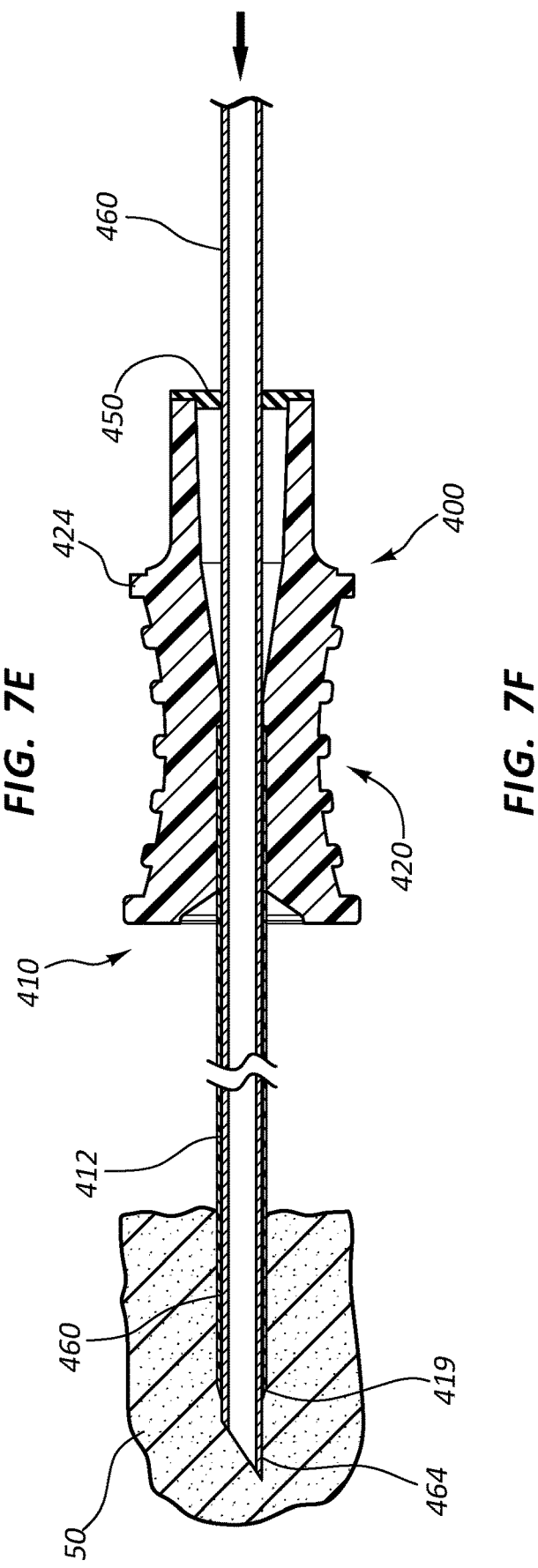
FIG. 7E
FIG. 7F

INTRODUCER SHEATH AND METHODS

RELATED APPLICATIONS

This application claims priority to U.S. Provisional Application No. 61/929,614 filed on Jan. 21, 2014 and titled "Introducer Sheath," which is hereby incorporated by reference in its entirety.

TECHNICAL FIELD

The present disclosure relates generally to medical devices. More specifically, the present disclosure relates to devices that facilitate access to body tissue and/or fluid. For example, a sheath may be configured to introduce an elongate member into a patient. In some embodiments, the access device is configured to prevent fluid from passing through the access device during operation. Certain embodiments may also be configured to facilitate the disengagement of an introducer sheath from an elongate member, such as a trocar or needle, that is configured to be inserted into the introducer sheath.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 7A is a cross-sectional side view of a portion of an introducer sheath assembly in a first configuration.

FIG. 7B is a cross-sectional side view of a portion of the introducer sheath assembly of FIG. 7A in a second configuration.

FIG. 7C is a cross-sectional side view of a portion of the introducer sheath assembly of FIG. 7A in a third configuration.

FIG. 7D is a cross-sectional side view of a portion of the introducer sheath assembly of FIG. 7A in a fourth configuration.

FIG. 7E is a cross-sectional side view of a portion of the introducer sheath assembly of FIG. 7A in a fifth configuration.

FIG. 7F is a cross-sectional side view of a portion of the introducer sheath assembly of FIG. 7A in a sixth configuration.

DETAILED DESCRIPTION

Figure 1:
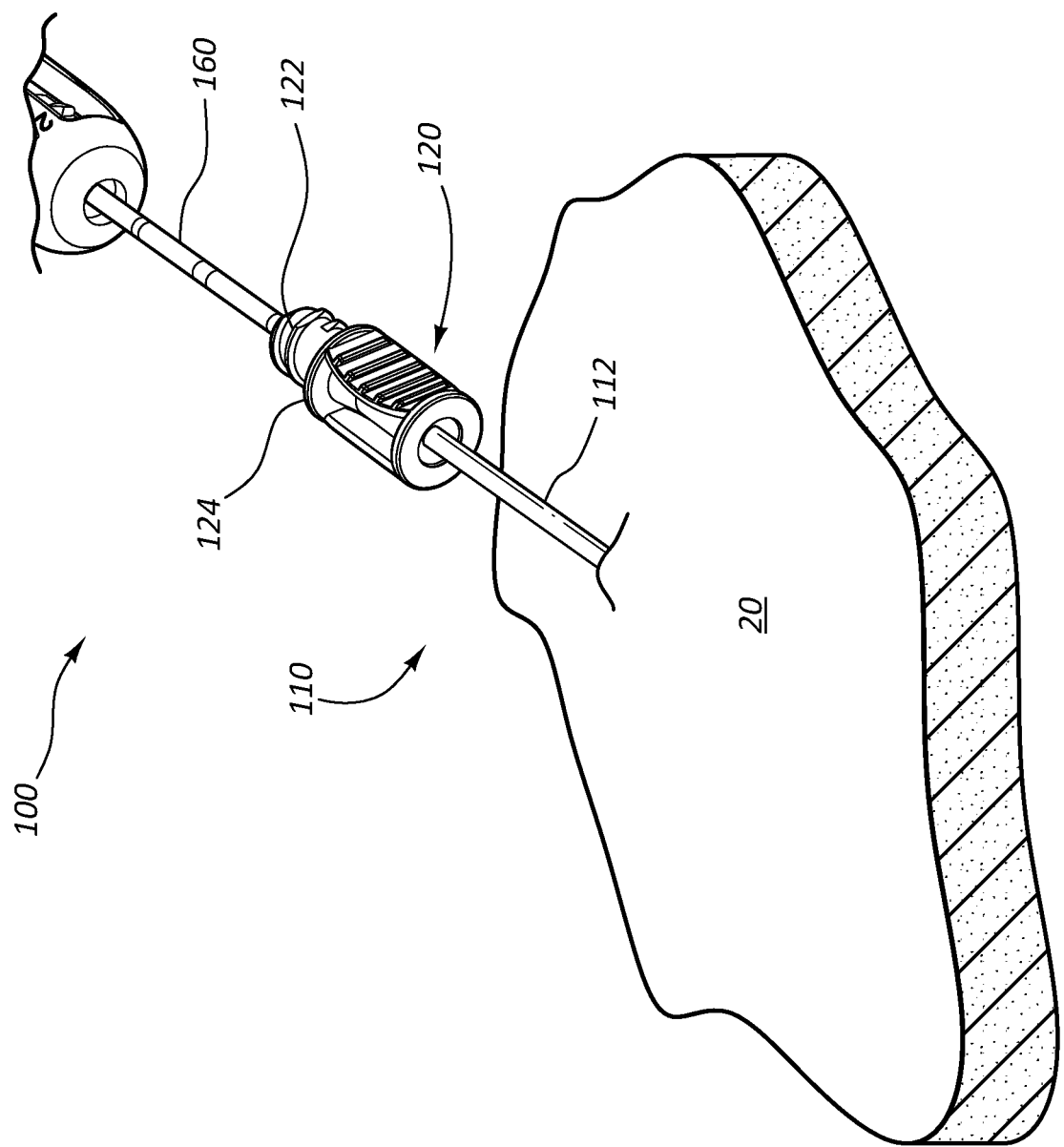
FIG. 1 is a perspective view of an access device that has been inserted into a patient.

A patient's internal tissue and/or fluid may be accessed during various medical procedures. Access devices may be configured to facilitate access to tissues and/or fluids during such procedures. For example, an access device may comprise a lumen, at least a portion of which may be disposed within a patient. The lumen may be used as a conduit for delivering medicaments and/or as a sheath that facilitates the insertion of needles or other elongate members. In some embodiments, the access device is configured to protect tissue situated adjacent to the access device from contamination. For example, as a needle or other elongate member is withdrawn from a patient through an access device, the lumen of the access device prevents material that is carried by the needle or other elongate member from contacting at least a portion of the tissue situated adjacent the device. In some embodiments, access devices, such as an introducer sheath, may be used during a biopsy procedure.

During a biopsy, a practitioner may obtain tissue and/or fluid samples from the patient. Biopsy samples may be obtained from various locations within a patient's body. For example, among other locations, medical practitioners may obtain biopsy samples from the liver, the bladder, the gastrointestinal tract, the prostate, breasts, lymph nodes, muscle, skin, or lungs.

During a biopsy procedure, a practitioner may insert an introducer sheath into a patient. The introducer sheath may comprise an elongate member, such as a cylindrical tube, with a lumen that extends through the elongate member. Insertion of the introducer sheath into the patient may be facilitated by first inserting a second elongate member, such as a trocar, into the introducer sheath such that a pointed end of the trocar protrudes from the distal end of the introducer sheath. With the pointed end protruding from the introducer sheath, the trocar and the introducer sheath may together be inserted into the patient. Once the introducer sheath is positioned within the patient, the trocar may be withdrawn from the introducer sheath. At this stage of the procedure, the introducer sheath provides a conduit that allows access to a patient's internal body tissue and/or fluid. This conduit may be used to obtain tissue or fluid samples in the case of a biopsy, or the conduit may be used for other purposes (e.g., drug delivery). In a biopsy procedure, a cutting device (e.g., a needle or some other device configured to obtain body fluid and/or tissue samples) may then be inserted through the introducer sheath. The practitioner may then obtain a sample from the body and withdraw both the device and the sample from the introducer sheath.

Biopsies may be obtained for numerous reasons. Exemplary reasons for seeking a biopsy sample include testing for cancer or other diseases, monitoring response to therapy, or determining the stage of a disease or condition. Lung biopsies, in particular, may facilitate the diagnosis of cancer, sarcoidosis, pulmonary fibrosis, and severe pneumonia. Tests on biopsied samples may also reveal the presence of bacteria, viruses, or fungi.

In some instances, the patient may face a risk of infection from the biopsy procedure. Infection may arise from the patient's exposure to a non-sterile environment. One possible avenue of exposure is through an introducer sheath lumen, where the lumen places the patient's internal tissue in fluid communication with the external environment.

A biopsy patient also faces the risk that biopsy sample material will, to the patient's detriment, spread elsewhere in his or her body as a result of the procedure. For example, a needle may be inserted into a patient and manipulated to obtain a sample of diseased and/or cancerous material. In some instances, when the needle is subsequently withdrawn, such material may contact and/or deposit onto tissue situated adjacent to the path followed by the needle as it is withdrawn. In this manner, diseased and/or cancerous tissue may be inadvertently transported within the patient's body. By inserting the device used to obtain the biopsy sample through an introducer sheath, the risks associated with the inadvertent spread of body tissue and/or fluid from the biopsy site may be mitigated as the introducer sheath may surround a portion of the biopsy needle and prevent contamination as it is withdrawn.

Procedures involving access to the chest cavity, for example lung biopsies, pose another risk—a collapsed lung (pneumothorax). A lung may collapse when air collects in the pleural cavity that surrounds a lung. Air may enter into the pleural cavity by escaping from the patient's own lung or by entering through a conduit that places the pleural cavity and the external environment in fluid communication with each other. Several factors that may increase the risk of pneumothorax include the dwell time of the introducer sheath, puncture angles that are not perpendicular to the punctured surface, the diameter of the introducer sheath, and the depth and breadth of the inserted trocar and/or introducer sheath. The collapse of a lung via entry of air into the pleural cavity may prevent the lung from filling properly and lead to oxygen deprivation, low blood pressure, and/or death. In some circumstances, a chest tube or chest drain may be inserted to remove air from the pleural cavity.

The following exemplary procedure illustrates a possible scenario in which air may enter into a pleural cavity during a biopsy procedure. An introducer sheath with a trocar disposed within it is inserted into a patient. The trocar pierces a pleural membrane during insertion. The trocar is then withdrawn from the introducer sheath, leaving the distal end of the introducer sheath positioned adjacent to the pierced pleural membrane. With the trocar withdrawn, a lumen that extends through the introducer sheath places the pleural cavity in fluid communication with the external environment. Air from the external environment may thus enter into the pleural cavity through the introducer sheath. The practitioner may then insert a biopsy needle through the introducer sheath to obtain a sample of pleural tissue. The device is then withdrawn from the introducer sheath, which again allows air to pass through the introducer sheath into the pleural cavity.

Air from the external environment may enter into the pleural cavity during other procedures as well. For example, in an alternative procedure, the trocar does not pierce the pleural membrane as the introducer sheath is inserted into the patient's chest. Rather, the pleural membrane is pierced after the trocar has been removed, when an inserted biopsy needle pierces the membrane to obtain a tissue sample. Withdrawal of the biopsy needle places the pleural cavity in fluid communication with the external environment via the introducer sheath, allowing air to fill the pleural cavity.

As disclosed herein, the passage of air from the external environment into the patient (e.g., into the pleural cavity) may be impeded by a valve disposed adjacent to a lumen that extends through an introducer sheath. As used herein, a valve is disposed "adjacent to" a lumen if (1) the valve is disposed entirely within the lumen, (2) the valve is partially, but not wholly, disposed within the lumen, or (3) the valve is adjacent to, but does not lie within, the lumen. The valve may be configured to allow a portion of a second elongate member (e.g., a trocar, a needle, cutting device) to pass through the valve. Whether or not an elongate member is disposed across the valve, the valve may be configured to prevent or reduce fluid flow across the introducer sheath (i.e., from the external environment to the patient and vice versa). The valve may also prevent body tissue and fluid from being exposed to the nonsterile external environment.

It will be readily understood that the components of the embodiments as generally described and illustrated in the figures herein could be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrases "connected to" and "coupled to" refer to any form of interaction between two or more entities, including mechanical, electrical, magnetic, electromagnetic, fluid and thermal interaction. The phrase "fluid communication" is used in its ordinary sense, and is broad enough to refer to arrangements in which a fluid (e.g., a gas or a liquid) can flow from one element to another element when the elements are in fluid communication with each other.

The directional terms "proximal" and "distal" are used herein to refer to opposite locations on a component or device. The proximal end of a component or device is defined as the end of the device closest to the practitioner when the device is in normal use by the practitioner. The distal end is the end opposite the proximal end, along the longitudinal direction of the device, or the end furthest from the practitioner during normal use. As used herein, "needle" or "biopsy needle" refers to any device configured to withdraw a tissue or fluid sample from a patient (e.g., a hollow needle or an otherwise solid needle with a cutting or sectioning portion such as a trough). The term "substantially perpendicular" refers to angles that are perpendicular to the reference surface or angles that deviate from being perpendicular to the reference surface by 5° or less. The term "detent," as used herein, refers to a multicomponent connection that restricts the relative movement of separable components via frictional engagement. Such multicomponent connections may comprise ridges, catches, protrusions, depressions, etc. As used, herein, "vascular procedures" are procedures in which an introducer sheath is longitudinally inserted into a patient's vasculature (e.g., intravenous applications). All other procedures are "non-vascular."

FIG. 1 is a perspective view of a medical device 100, the distal end of which has been inserted into patient tissue and/or fluid 20. As illustrated in FIG. 1, the medical device 100 may comprise an introducer sheath 110 and a needle 160 configured to be disposed within the introducer sheath 110. The introducer sheath 110 may be configured to facilitate access to body tissue and/or fluid, for example percutaneous access to body tissue. In some embodiments, the introducer sheath is configured for use in non-vascular procedures (e.g., a lung biopsy). The introducer sheath may comprise a rigid (e.g., steel or other metal) hypotube that is configured to facilitate percutaneous access to lung tissue. Such a device may not be configured for vascular access as a rigid sheath may tend to damage the vasculature if it were inserted longitudinally into a vein or artery due to its hardness and rigidity. The needle 160 may be configured to obtain samples of body tissue or fluid 20 from within a patient.

In some biopsy procedures, the introducer sheath 110 is initially inserted and/or otherwise positioned in a patient's tissue and/or fluid 20. Subsequently, the needle 160 is inserted into a lumen of the introducer sheath 110. The needle 160 may emerge from the introducer sheath 110 to obtain a sample of tissue, for example, from a position adjacent the distal tip of the introducer sheath 110. As shown in FIG. 1, the introducer sheath 110 may comprise an introducer sheath hub 120, a ridge 124, and/or threads 122, which may be configured to couple the introducer sheath 110 to an elongate member. Analogous components, as well as methods for using these components to couple an introducer sheath to an elongate member, will be further discussed in connection with other figures.

In the configuration illustrated in FIG. 1, the medical device 100 is inserted into patient tissue and/or fluid 20 at an angle that is not perpendicular to the surface of the patient's skin. However, in some procedures, the medical device and/or components of the medical device (e.g., an introducer sheath, needle, or trocar) are inserted at an angle that is perpendicular or substantially perpendicular to the surface of the patient's skin or to the surface of the tissue within the patient that is to be sampled.

FIGS. 2A-4 depict another embodiment of a medical device 200 that resembles the medical device 100 described above in certain respects. Accordingly, like features are designated with like reference numerals, with the leading digits incremented to "2." For example, the embodiment depicted in FIGS. 2-4 includes an introducer sheath 210 that may, in some respects, resemble the introducer sheath 110 of FIG. 1. Relevant disclosure set forth above regarding similarly identified features thus may not be repeated hereafter. Moreover, specific features of medical devices and related components shown in FIGS. 2A-4 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the medical devices and related components of FIG. 2A-4. Any suitable combination of the features, and variations of the same, described with respect to the medical device and components illustrated in FIG. 1, can be employed with the medical device and components of FIGS. 2A-4, and vice versa. This pattern of disclosure applies equally to further embodiments depicted in subsequent figures and described hereafter, wherein the leading digits may be further incremented.

Figure 2:
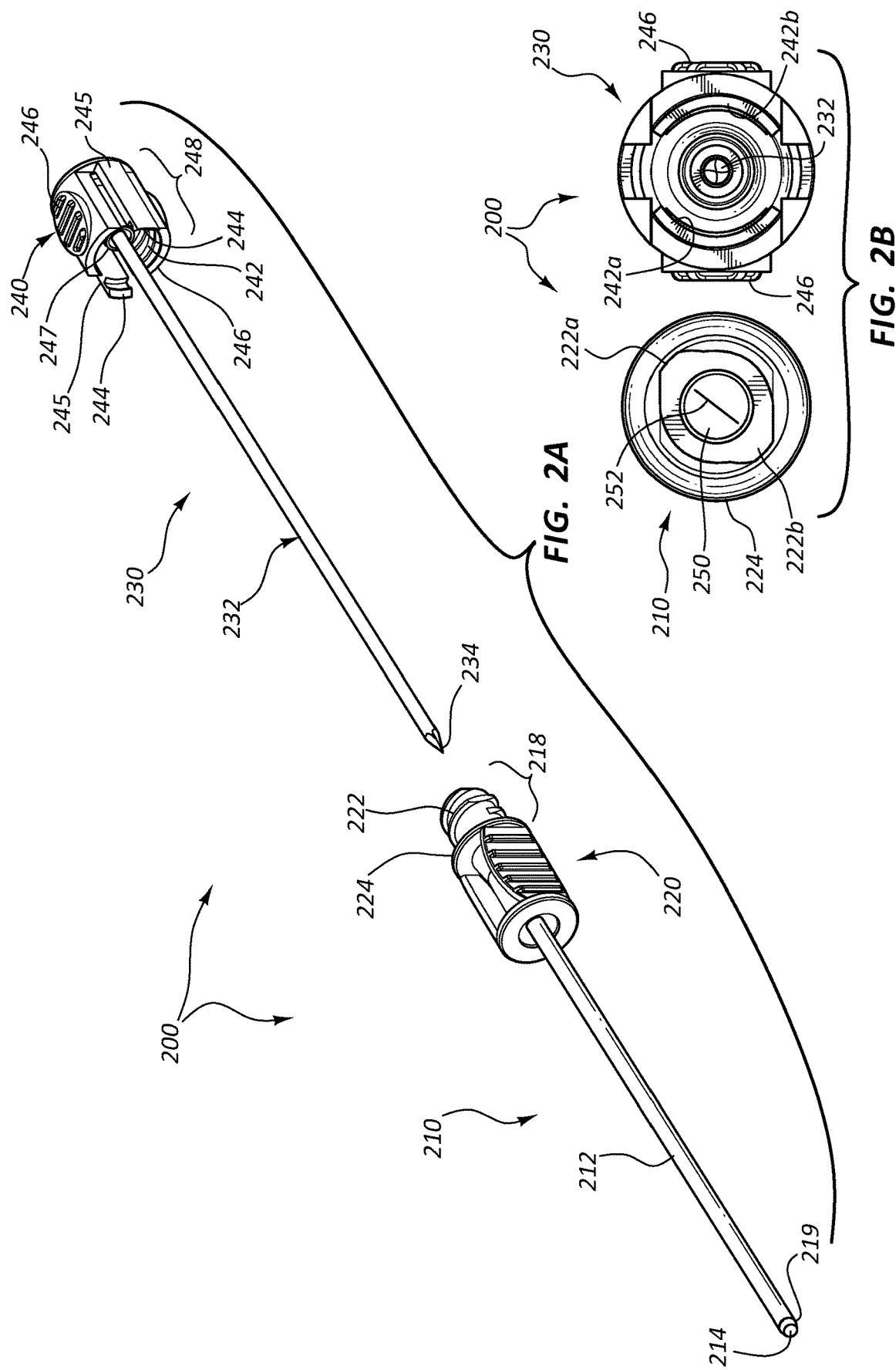
FIG. 2A is a perspective view of an introducer sheath and an elongate member in a first configuration.
FIG. 2B is an end view of the introducer sheath and elongate member of FIG. 2A with the proximal end of the introducer sheath and the distal end of the elongate member facing out of the page.
Figure 3:
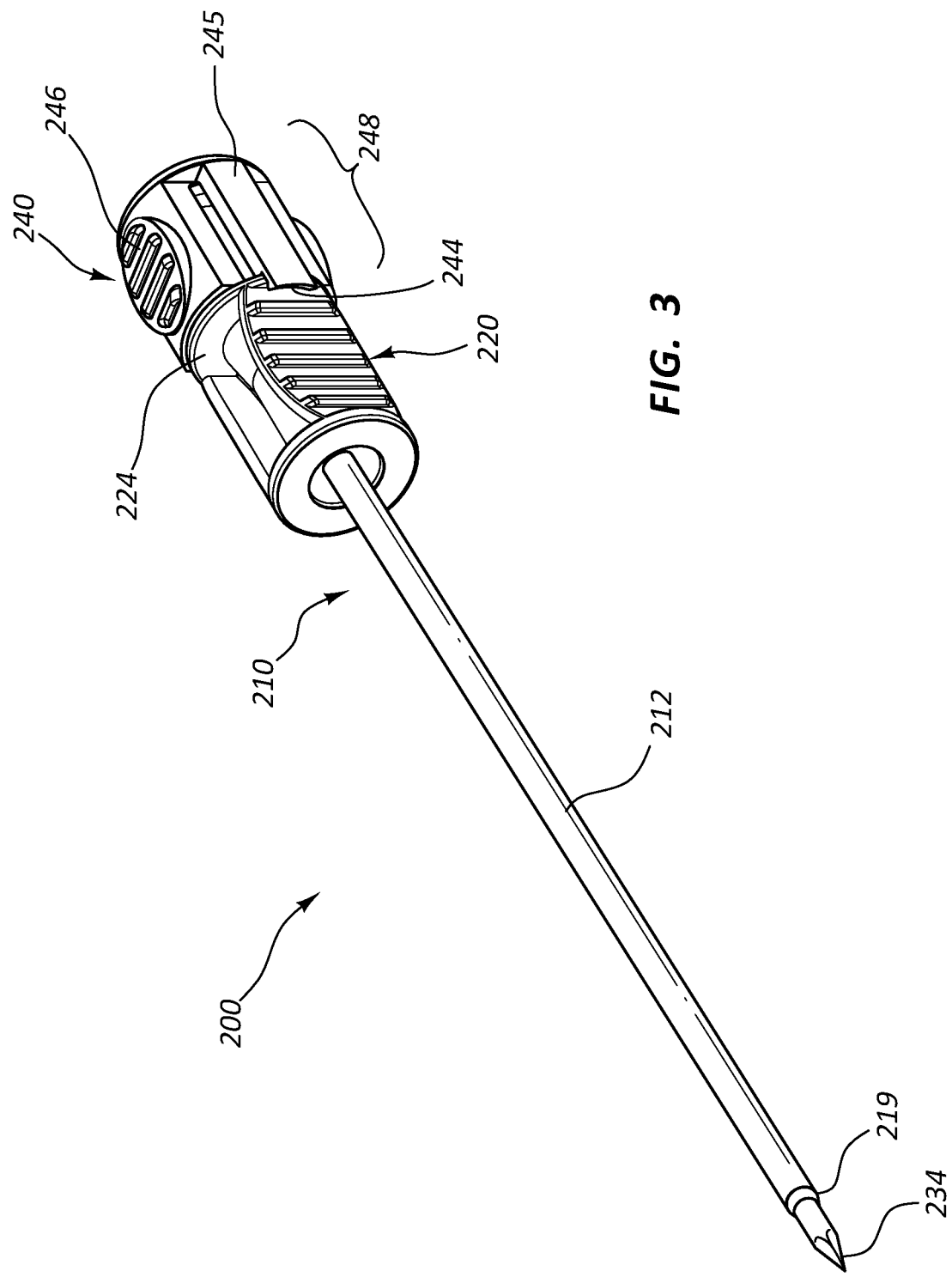
FIG. 3 is a perspective view of the elongate member and introducer sheath of FIG. 2A in a second configuration.
Figure 4:
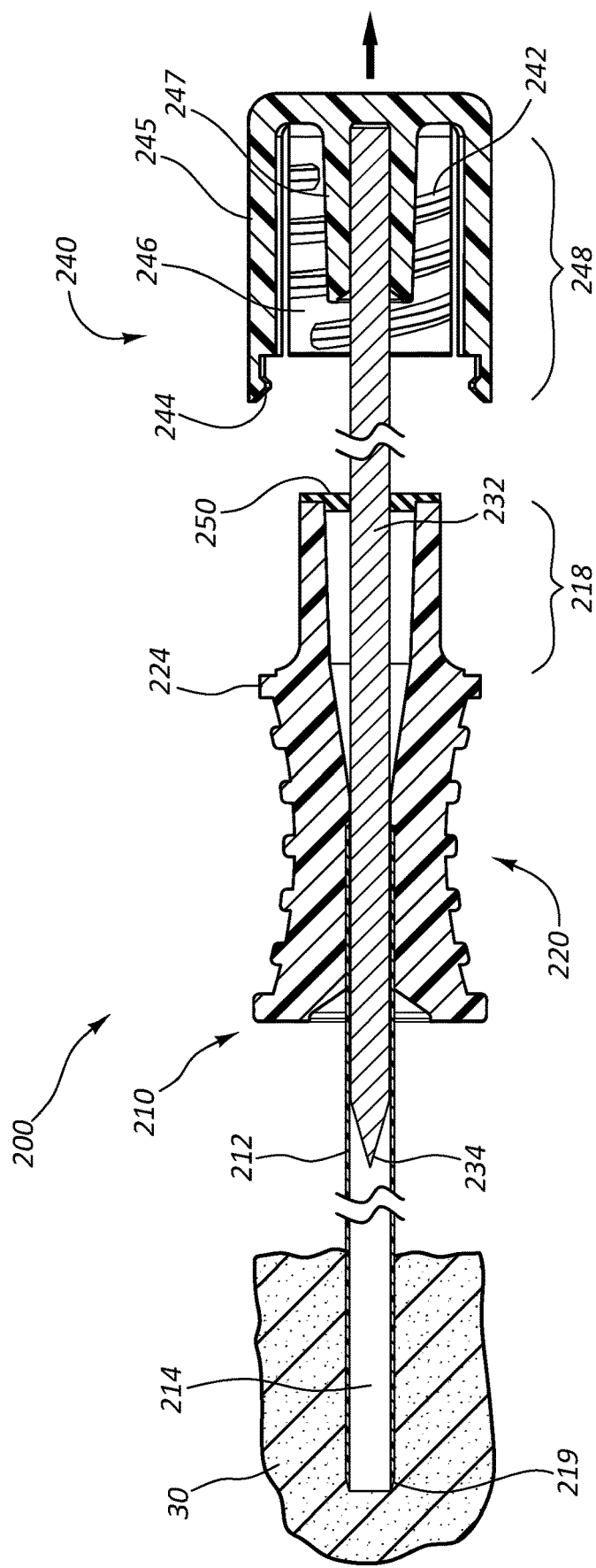
FIG. 4 is a cross-sectional side view of the introducer sheath and elongate member of FIG. 2A in a third configuration.

FIGS. 2A-4 provide various views of the medical device 200. In particular, FIGS. 2A and 3 provide perspective views of the medical device 200 in a first and second configuration, respectively. FIG. 2B provides end views of two components of the medical device 200, and FIG. 4 provides a cross-sectional view of the medical device 200.

The medical device 200 may comprise an introducer sheath 210, a second elongate member 230, and a lumen 214. The second elongate member 230 may comprise a trocar 232 that is configured to be at least partially disposed within a lumen 214 of the introducer sheath 210. In other embodiments, the second elongate member 230 may alternatively or additionally comprise other elongate instruments, such as biopsy needles, injection needles, cutting devices and so forth. As shown in FIG. 3, when the second elongate member 230 is fully inserted into the introducer sheath 210, the distal tip 234 of the trocar 232 may emerge from the distal end 219 of the introducer sheath 210. With the trocar 232 disposed within the introducer sheath 210, the trocar 232 and introducer sheath 210 may be inserted as a single unit into a patient. The pointed distal tip 234 of the trocar 232 may be configured to pierce the patient's skin and tissue as the trocar 232 and introducer sheath 210 are inserted into the patient. In this manner, the placement of the introducer sheath 210 within the patient may be facilitated.

As shown in FIGS. 2A-4, the introducer sheath 210 may comprise an introducer sheath hub 220 and a first elongate member 212. A lumen 214 may extend through the first elongate member 212, along the longitudinal length of the elongate member 212. The lumen 214 may also extend through the introducer sheath hub 220. The lumen 214 may be configured to have a size and shape that accommodates at least a portion of a trocar, needle or other elongate instrument.

The introducer sheath hub 220 may be disposed adjacent a proximal end of the first elongate member 212 and may be configured to selectively couple to the second elongate member 230. In some scenarios, a trocar 232 and introducer sheath 210 may be coupled to each other and together inserted into a patient. In the embodiment shown in FIGS. 2A-4, the introducer sheath hub 220 comprises a ridge 224 and threads 222. In this embodiment, both the ridge 224 and threads 222 are configured to releasably couple the introducer sheath 210 to a second elongate member 230. In other embodiments, the introducer sheath hub may comprise only a ridge (and no threads) or threads (and no ridge), or some other coupling feature. While ridge 224 of the illustrated embodiment comprises an annular protrusion from the introducer sheath hub 220, in other embodiments, a ridge or ridges may extend around only a portion of an introducer sheath hub's circumference. Further, in certain embodiments, recesses, protrusions, edges, or other features of the introducer sheath hub 220 may be configured to interact with components of the second elongate member 230 when coupling the introducer sheath hub 220 to the second elongate member 230.

The second elongate member 230 may comprise a trocar 232 and a second elongate member hub 240. The trocar 232 may be configured to be disposed within the lumen 214 of introducer sheath 210. The trocar 232 may comprise a distal tip 234 that extends from the distal end 219 of the introducer sheath 210 when the second elongate member 230 is fully inserted into the introducer sheath 210. Features or components of the second elongate member hub 240 may be configured to interact with another component, such as the introducer sheath hub 220, to facilitate coupling of the second elongate member hub 240 to the additional component. For example, the second elongate member hub 240 may comprise catches 244, depressible members 246, and a distal region 248 configured to frictionally engage the proximal end 218 of the introducer sheath hub 220 (e.g., by engaging one or more mating detent features on the proximal end 218).

In the embodiment shown in FIGS. 2A-4, as the second elongate member 230 is advanced through the introducer sheath 210, the second elongate member hub 240 may approach the introducer sheath hub 220. These hubs may be configured to engage with and/or couple to each other via multiple mechanisms or connections.

For example, the introducer sheath hub 220 and the second elongate member hub 240 may be configured to engage with each other via a snap fit-type mechanism. In the embodiment shown in FIGS. 2A-4, full insertion of the second elongate member 230 into the introducer sheath 210 causes the catches 244 of the tabs 245 to be advanced over the ridge 224 of the introducer sheath hub 220. By inserting the second elongate member in this manner, the catches 244 may "snap" over the ridge 224 to create a snap fit-type connection. Thus, when snapped in place, the catches 244 and ridge 224 may impede withdrawal of the second elongate member 230 from the introducer sheath 210. In this manner, when the second elongate member 230 is fully inserted into the introducer sheath 210, the catches 244 and the ridge 224 together form a detent 224, 244. The detent 224, 244 shown in FIG. 3 releasably couples the introducer sheath 210 to the second elongate member 230. In some embodiments, a ridge and catch (or other detents) may be disengaged via actuation of a release mechanism (e.g., depression of a depressible member or members). In the embodiment depicted in FIGS. 2A-4, depression of depressible members 246 that are disposed on opposite sides of the second elongate member hub 240 causes the catches 244 to disengage from the ridge 224 of the introducer sheath 210. In particular, depression of the depressible members 246 causes the distal end of tabs 245 to be displaced radially from the longitudinal axis of the second elongate member 230 such that catches 244 may be freely inserted over or freely withdrawn from ridge 224 of the introducer sheath 210.

The particular components of the introducer sheath hub 220 and second elongate member hub 240 are exemplary. In other embodiments, the introducer sheath hub and the second elongate member hub may comprise components that differ from those disclosed in FIGS. 2A-4. For example, in one embodiment, the second elongate member hub may comprise a ridge while the introducer sheath hub comprises a catch configured to frictionally engage with the ridge. Additionally numerous other mechanisms for creating a snap fit-type connection between the introducer sheath hub and the second elongate member hub are within the scope of this disclosure. Such mechanisms include components such as portions of detents, bumps, protrusions, catches, dogs, pivoting members, holes, and recesses that are configured to interact with one another to restrict the relative movement of multiple components. In some embodiments, one or more of these features will extend around the entire circumference of the introducer sheath hub or the second elongate member hub. In other embodiments, one or more of these features will extend around only a portion of the circumference of the hubs. Thus, sets of hubs that are configured to selectively engage with one another by at least a snap-fit type connection, yet differ from those shown in FIGS. 2A-4, are within the scope of this disclosure.

The introducer sheath hub 220 and the second elongate member hub 240 may also be configured to engage with each other via frictional engagement of a protrusion 247 of the second elongate member 230 with at least a portion of the lumen 214. In particular, as the second elongate member hub 240 approaches and engages with the introducer sheath hub 220, the protrusion 247 may be inserted into and frictionally engage the lumen 214. In some embodiments, the protrusion 247 and the lumen 214 may be tapered such that the protrusion 247 and the lumen 214 engage with one another along a mating taper. Further, in some embodiments, the frictional engagement of protrusion 247 with the lumen 214 may be overcome by exerting opposing forces on the introducer sheath hub 220 and the second elongate member hub 240.

The introducer sheath hub 220 and the second elongate member hub 240 may additionally or alternatively be configured to engage with each other via threads. As depicted in FIG. 2A, the proximal end 218 of the introducer sheath 210 comprises threads 222, and the second elongate member hub 240 comprises threads 242. An alternative view of the threads 222, 242 may be found in FIG. 2B, which provides an end view of the introducer sheath 210 and the second elongate member 230 of FIG. 2A with the proximal end of the introducer sheath 210 and distal end of the second elongate member 230 facing out of the page. As shown in this view, introducer sheath hub threads 222 comprise noncontiguous thread portions 222a and 222b, which are oppositely positioned around the proximal end 218 of the introducer sheath 210. Similarly, noncontiguous thread portions 242a and 242b may be oppositely positioned around the second elongate member hub 240.

The second elongate member hub threads 242 and the introducer sheath hub threads 222 may be configured such that the introducer sheath hub 220 and second elongate member hub 240 may more fully engage by rotating the threads 242, 222 relative to each other. For example, if the introducer sheath hub threads 222 and the second elongate member hub threads 242 are circumferentially aligned as they approach one another (e.g., the orientation shown in FIG. 2A where both threads 222 and 242 are vertically aligned with the ground), the introducer sheath hub threads 222 will contact second elongate member hub threads 242, preventing further insertion of the second elongate member 230. However, if the introducer sheath hub threads 222 and the second elongate member hub threads 242 are circumferentially offset as they approach one another (e.g., with the introducer sheath hub threads 222 aligned vertically and second elongate member hub threads 242 aligned horizontally with respect to the ground), the second elongate member hub 240 may more fully engage with the introducer sheath hub 220. After the second elongate member hub 240 has approached the introducer sheath hub 220 with the threads 242 of the second elongate member hub 240 circumferentially offset from the threads 222 of the introducer sheath hub 220, the second elongate member hub 240 may be rotated relative to the introducer sheath hub 220 such that the introducer sheath hub threads 222 and second elongate member hub threads 242 engage with each other. As rotation while the threads 222, 242 are engaged may also longitudinally displace the second elongate member 230 with respect to the introducer sheath 210 (due to interaction of the threads), this rotation of the second elongate member hub 240 relative to the introducer sheath hub 220 may also advance the second elongate member 230 with respect to the introducer sheath 210. In some embodiments, the components may be configured such that when the threads are fully engaged, the second elongate member 230 is fully extended into the introducer sheath 210 and/or the components are disposed such that the catches 244 and ridge 224 are also engaged. The reverse of this process may be used to disengage the threads 222, 242 from one another.

The embodiment disclosed in FIGS. 2A-4 is configured to facilitate the engagement of the introducer sheath hub 220 with the second elongate member hub 240 via at least three mechanisms: (1) a snap fit-type mechanism (e.g., the engagement of catches 244 with a ridge 224), (2) a frictional engagement mechanism (e.g., the engagement of the protrusion 247 with the lumen 214) and (3) a thread engagement mechanism (e.g., the engagement of introducer sheath threads 222 with second elongate member hub threads 242). Embodiments wherein any sub combination of any of these three engagement mechanisms are present are also within the scope of this disclosure. Further, other embodiments may comprise additional coupling mechanisms. For example, a medical device may comprise only a snap fit-type mechanism, a thread engagement mechanism, or a friction-fit mechanism for engaging the hubs. Alternatively, a medical device may comprise any two of these engagement mechanisms. In some embodiments, hubs may be uncoupled from each other by any combination of depressing a depressible button, exerting opposing forces on the hubs, and/or rotating one hub relative to the other hub. Additionally, in some embodiments the hubs may disengage from each other via a process that does not include rotation of one hub relative to the other hub. For example, in an embodiment where the medical device comprises a ridge and catches but does not comprise threads, an introducer sheath may be disengaged from the second elongate member hub without rotating the second elongate member hub relative to the introducer sheath.

In some embodiments, the second elongate member hub may be disengaged and withdrawn from the introducer sheath hub using a single hand. For example, from a position in which the introducer sheath hub and the hub of the second elongate member are fully engaged, the practitioner may, with one hand, actuate a release mechanism (e.g., depress a depressible button) that causes the catches of the second elongate member hub to be radially displaced relative to the longitudinal axis of the second elongate member. With the catches displaced in this manner, the practitioner may exert a proximal force on the second elongate member hub with the same hand. In embodiments where the frictional forces between the second elongate member and the introducer sheath are sufficiently low, this proximal force may overcome such frictional forces and allow the second elongate member to be withdrawn from the introducer sheath without immobilizing the introducer sheath with a second hand. Embodiments without threads may facilitate such one-handed uncoupling of the second elongate member from the introducer sheath. In embodiments where the introducer sheath and second elongate member are coupled to one another by threads, one-handed uncoupling may also comprise rotating the second elongate member relative to the introducer sheath.

FIG. 4 is a cross-sectional side view of the medical device 200 of FIGS. 2A, 2B, and 3, with the distal tip 219 of the introducer sheath 210 disposed within patient tissue and/or fluid 30. As depicted, a lumen 214 extends through both the first elongate member 212 and the introducer sheath hub 220. The lumen 214 may have a larger circumference (or otherwise extend further from the longitudinal axis of the introducer sheath 210) at the proximal end 218 of the introducer sheath 210 than at the distal end 219 of the introducer sheath 210. The larger circumference of the lumen 214 at its proximal end may allow it to frictionally engage a protrusion 247 of the second elongate member hub 240 when the second elongate member 230 is fully inserted into the introducer sheath 210.

FIG. 4 also discloses a valve 250 disposed adjacent to the lumen 214. As shown in FIG. 4, the valve 250 is directly coupled to the introducer sheath hub 220. The valve 250 may comprise a slit 252 or other opening configured to allow traversal of the valve 250 by at least a portion of the second elongate member. In other embodiments, the second elongate member may traverse a valve without a slit (e.g., an elastomeric septum). The valve 250 may comprise material (e.g., an elastomer) that conforms to the contours of the second elongate member to form a seal around the second elongate member.

For example, the distal end of a needle or trocar may pass through the valve. The valve 250 may impede the flow of fluid across the valve both (1) when an elongate member is disposed across the valve (e.g., the valve forms a seal around the elongate member that prevents fluid flow around the elongate member) and (2) when no elongate member traverses that valve. Thus, when the second elongate member 230 is fully withdrawn from both the introducer sheath 210 and the valve 250, air or other fluid may be unable to pass through the lumen 214 of the introducer sheath 210 and interact with the patient's body tissue or fluid 30. Likewise fluid flow from the patient to the external environment may be impeded as well.

As shown in FIG. 4, the valve is disposed at the most proximal end of the introducer sheath 210. However, the valve may be disposed at other locations adjacent to or within the lumen. Additionally, in some embodiments, multiple serially disposed valves may be disposed within and/or adjacent to the lumen.

With reference to the arrow shown in FIG. 4, the trocar 232 may be withdrawn from the introducer sheath 210, allowing for subsequent insertion of a biopsy needle or other medical device.

Figure 5:
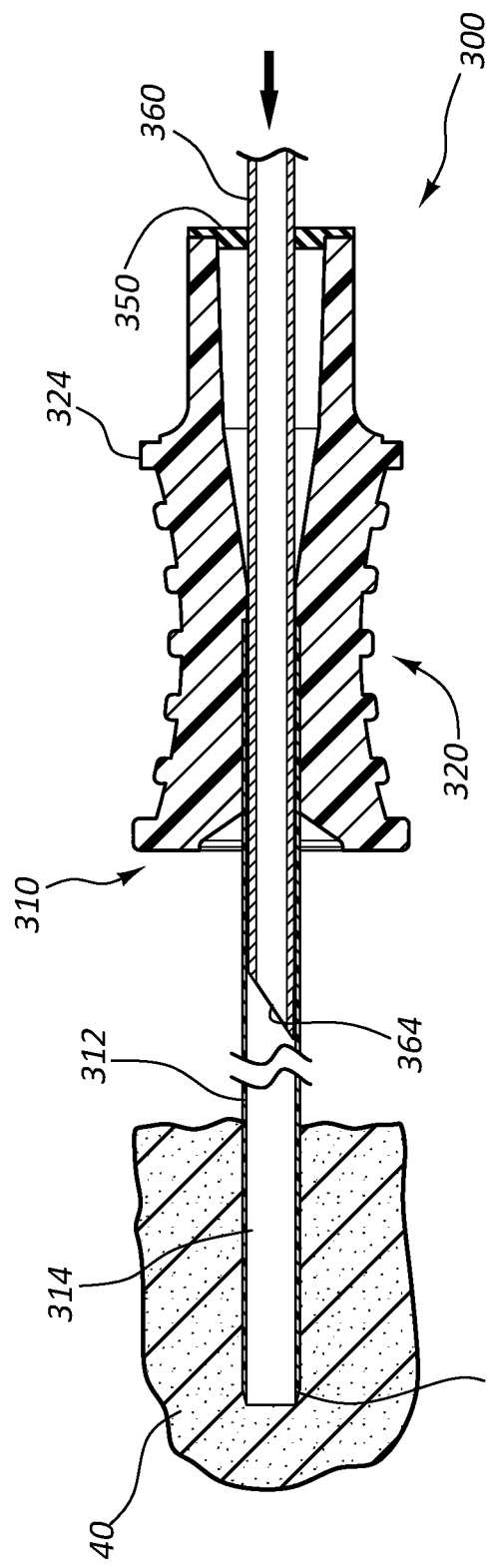
FIG. 5 is a cross-sectional side view of an introducer sheath, body tissue, and a needle in a first configuration.
Figure 6:
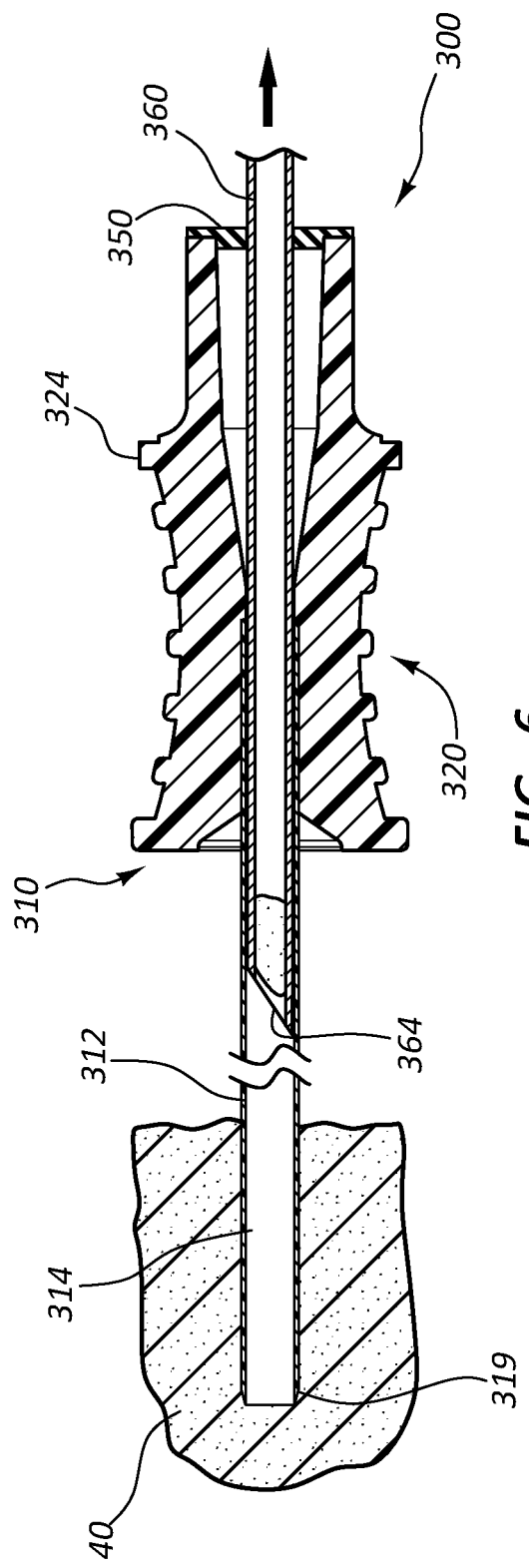
FIG. 6 is a cross-sectional side view of the introducer sheath, body tissue, and needle of FIG. 5 in a second configuration.

FIGS. 5 and 6 depict another embodiment of a medical device 300. In particular, FIG. 5 discloses a needle 360, an introducer sheath 310, and body tissue or fluid 40 in a first configuration, and FIG. 6 discloses the same elements in a second configuration. FIG. 5 discloses a needle 360 that is being inserted through an introducer sheath 310 into a patient to retrieve body tissue and/or body fluid 40 from the patient. The depicted needle 360 is a cylindrical needle comprising a hollow tube. However, other needles may be used. For example, a biopsy device comprising a partial core needle (e.g., a solid core needle that comprises troughs or recesses in an outside diameter of the needle), a full core needle (e.g., a needle assembly comprising two or more coaxial tubular needles configured to cut full core tissue from the patient), or any other elongate instrument, including those configured to cut or displace a tissue sample, may also be employed. Various biopsy devices may be used in connection with the introducer and other components disclosed herein. For example, U.S. patent application Ser. No. 14/157,935, filed on Jan. 17, 2014 and titled "Impact Biopsy Device and Method of Use," which is hereby incorporated by reference in its entirety, discloses biopsy devices that may be used in connection components disclosed herein.

As shown in FIG. 5, the distal tip 334 of the needle 360 passes through the valve 350 and enters into the introducer sheath 320. As a portion of the needle 360 passes through the valve 350, the valve 350 may conform to the contours of the needle 360, preventing fluid from passing through the valve. Once a portion of the needle 360 has passed through the valve 350, the practitioner may then use the needle 360 to obtain a tissue sample. In some circumstances, at least the distal end 334 of the needle 360 emerges from the distal end 319 of the introducer sheath 310 to obtain the tissue or fluid sample 40.

Subsequently, as shown in FIG. 6, the needle 360 may be withdrawn from the introducer sheath 310. As depicted in FIG. 6, the desired tissue sample passes through both (1) the introducer sheath lumen 314 and (2) the valve 350. The elongate member 312 and other components of the introducer sheath 310 may prevent tissue or fluid 40 that is being withdrawn from the patient from contacting tissue or fluid disposed adjacent the elongate member 312 as the sample is being withdrawn. Additionally, the valve 350 may be configured to seal around the needle 360 as the needle 360 is withdrawn from the introducer sheath 310. Thus, both while the needle is being withdrawn and subsequent to its withdrawal, the valve may prevent the flow of fluid across the valve.

FIGS. 7A-7G are cross-sectional side views of an introducer sheath assembly in seven configurations, with each configuration corresponding to a position of the assembly during an exemplary procedure. Analogous procedures may or may not proceed through each configuration depicted. Additionally, analogous procedures may include configurations or steps not shown in FIGS. 7A-7G. Procedures with any sub-combination of the steps below are within the scope of this disclosure.

FIG. 7A shows an introducer sheath 410 and a second elongate instrument 430 with the second elongate instrument 430 disposed outside the introducer sheath 410. In the illustrated embodiment, the second elongate instrument 430 comprises a trocar 432 and a second elongate member hub 440. The trocar 432 may be configured to be inserted into the introducer sheath 410. As the trocar 432 is advanced, the tip of the trocar 434 may pass through the valve 450. With the trocar 432 disposed across the valve 450, the valve 450 may seal around the trocar 432, preventing the passage of air or other fluid across the valve 450. The trocar 432 may then be coupled to a second elongate member hub 440 that is configured to releasably engage with an introducer sheath hub 420.

With reference to the view shown in FIG. 7A, to fully engage the second elongate member 430 with the introducer sheath 410, the practitioner may first rotate the second elongate member 430 approximately 90 degrees about the longitudinal axis of the second elongate member 430. The second elongate member hub 440 may subsequently be inserted or nearly fully inserted into the introducer sheath hub 420. The second elongate member hub 440 may then be rotated approximately 90 degrees such that threads 442 engage with threads (not shown in this view) on the introducer sheath hub 420.

FIG. 7B shows the trocar 432 fully disposed within the introducer sheath 410 and the second elongate member hub 440 coupled to the introducer sheath hub 420. In this fully engaged configuration, with the second elongate member 430 fully disposed within the introducer sheath 410, the trocar 432 traverses the valve 450, the catches 424 engage with the ridge 444, the protrusion 447 frictionally engages with the lumen 414, and the threads 442 of the second elongate member hub 440 engage with threads (not shown in this view) of the introducer sheath hub 420. In this configuration, the second elongate member 430 and the introducer sheath 410 may together be percutaneously inserted into a patient's tissue or fluid 50 such that the distal ends 434, 419 of the second elongate member 430 and the introducer sheath 410 are disposed within body tissue and/or fluid 50. In some scenarios, the introducer sheath is inserted such that it does not extend within and along a longitudinal length of a vascular lumen. The pointed distal end 434 of trocar 432, due to its ability to penetrate body tissue, may facilitate insertion of the first elongate member 412 of the introducer sheath 410.

FIG. 7C shows the trocar 432 and the introducer sheath 410 in a fully engaged configuration with the distal tips 434, 419 of the trocar 432 and introducer sheath 410 disposed within body tissue or fluid 50. From this fully engaged configuration, the second elongate member 430 may be withdrawn by, for example, (1) depressing the depressible members 446 such that catches 424 disengage from ridge 444, (2) rotating the second elongate member hub 440 relative to the introducer sheath hub 420 such that threads 442 disengage from threads on the introducer sheath hub 420, and (3) exerting a proximal force on the second elongate member hub 440 such that the frictional forces between protrusions 447 and the lumen 414 are overcome.

FIG. 7D depicts an introducer sheath 410 disposed within a patient's fluid or tissue 50. As shown in the illustrated embodiment, valve 450 lies adjacent to the lumen 414. Valve 450 may prevent the flow of fluid from the external environment into the patient and from the patient into the external environment. In the absence of such a valve, air may enter into a region of the patient and cause damage (e.g., infection, pneumothorax).

FIGS. 7E and 7F show a needle 460, the introducer sheath 410, and body tissue or fluid 50, with the needle 460 disposed either outside of the introducer sheath (FIG. 7E) or disposed across the introducer sheath 410 with a distal tip 464 disposed within the patient's tissue or fluid 50 (FIG. 7F). As indicated by the arrow shown in FIG. 7E, a practitioner may insert the needle 460 across the valve 450 and into the patient's tissue or fluid 50 to obtain a biopsy sample. For example, a practitioner may insert the needle across the valve 450 until the needle is disposed adjacent the distal end 419 of the introducer sheath 410. The practitioner may then manipulate the needle 460 to obtain a biopsy sample. For example, a practitioner may cause the tip 434 of the needle 460 to emerge from the distal tip 419 of the introducer sheath 410 such that fluid or tissue is disposed within the needle.

Figure 7G:
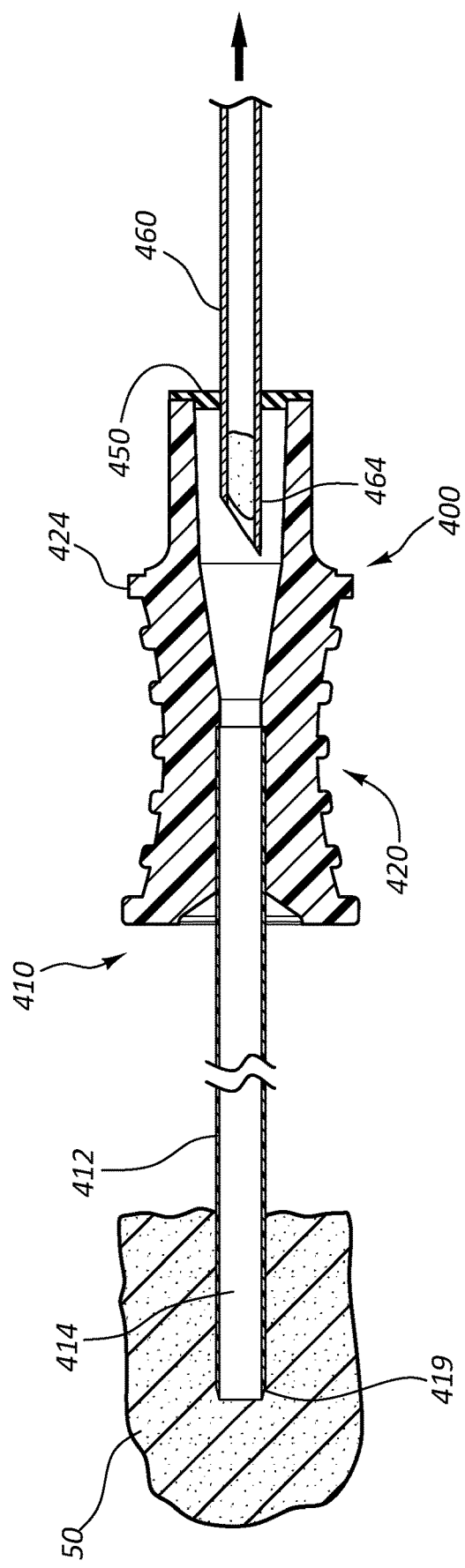
FIG. 7G is a cross-sectional side view of a portion of the introducer sheath assembly of FIG. 7A, in a seventh configuration.

FIG. 7G depicts a needle 460, an introducer sheath 410, and a biopsy sample with the biopsy sample disposed within the needle 460 and the distal tip 464 of the needle 460 disposed within the introducer sheath 410. As indicated by the arrow, a biopsy sample disposed within the needle 460 may be withdrawn from the introducer sheath 410. As the sample is withdrawn, elongate member 412 may prevent the biopsy sample from contacting tissue disposed along the longitudinal axis of the first elongate member 412. Additionally, the valve 450 prevents air and other fluids from crossing the valve 450 both while the needle 460 is being withdrawn and after the needle 460 has been withdrawn.

Any methods disclosed herein include one or more steps or actions for performing the described method. The method steps and/or actions may be interchanged with one another. In other words, the order and/or use of specific steps and/or actions may be modified with respect to the exemplary procedure outlined above. Moreover, sub routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. An introducer sheath for use during a percutaneous biopsy procedure, the introducer sheath comprising:
   a first elongate member;
   a lumen that extends through the first elongate member, the lumen configured to accommodate a first portion of the second elongate member;
   an introducer sheath hub disposed adjacent a proximal end of the first elongate member;
   a valve disposed adjacent to the lumen, the valve configured to allow traversal of the valve by a second portion of the second elongate member; and
   a second elongate member hub disposed adjacent to a proximal end of the second elongate member;
   wherein at least a portion of the valve is external to the introducer sheath hub;
   wherein the valve impedes fluid communication from the lumen across the valve;
   wherein a portion of the lumen distal of the valve is configured to frictionally engage a protrusion of the second elongate member;
   wherein the protrusion is disposed within the second elongate member hub;
   wherein the introducer sheath hub comprises an external ridge;
   wherein the second elongate member hub comprises an external catch;
   wherein the external catch engages with the external ridge when the second elongate member hub is coupled to the introducer sheath hub.

2. The introducer sheath of claim 1, wherein the introducer sheath hub is configured to selectively couple to the second elongate member and wherein the lumen extends through the introducer sheath hub.

3. The introducer sheath of claim 2, wherein the introducer sheath hub is configured to selectively couple to the second elongate member via a snap fit-type connection.

4. The introducer sheath of claim 3, wherein the first elongate member is configured to disengage from the second elongate member in response to actuation of a release mechanism.

5. The introducer sheath of claim 4, wherein the release mechanism comprises one or more depressible members.

6. The introducer sheath of claim 5, wherein the first elongate member is configured to disengage from the second elongate member without rotation of the first elongate member relative to the second elongate member.

7. The introducer sheath of claim 1, wherein
   the first elongate member comprises a rigid hypotube; and
   the introducer sheath is not configured for use in vascular procedures.

8. The introducer sheath of claim 1, wherein the portion of the lumen distal of the valve comprises a smooth taper, tapering inwardly from a proximal portion of the lumen having a larger diameter than a distal portion diameter of the lumen;
   wherein the protrusion comprises a smooth taper, tapering inwardly from a proximal portion of the protrusion having a larger diameter than a distal end diameter of the protrusion; and
   wherein the smooth taper of the lumen distal of the valve and the smooth taper of the protrusion frictionally engage each other when the introducer sheath hub is coupled to the second elongate member hub.

9. A hub assembly for selectively coupling two components of a medical device, the hub assembly comprising:
   a first component comprising a first lumen and a proximal end;
   a valve disposed adjacent to the first lumen, wherein at least a portion of the valve is disposed on an external surface of the proximal end of the first component; and
   a second component comprising:
      a distal region configured to frictionally engage the proximal end of the first component, wherein disposition of the distal region of the second component into engagement with the proximal end of the first component couples the second component to the first component via a snap fit-type connection; and
      a distal protrusion configured to frictionally engage the first lumen,
   wherein the distal protrusion is disposed within the second component;
   wherein a portion of the first lumen distal of the valve comprises a smooth taper, tapering inwardly from a proximal portion having a larger diameter to a distal portion diameter;
   wherein the distal protrusion comprises a smooth taper, tapering inwardly from a proximal portion having a larger diameter to a distal end diameter; and
   wherein the smooth taper of the first lumen distal of the valve and the smooth taper of the distal protrusion frictionally engage each other when the first component is coupled to the second component.

10. The hub assembly of claim 9, wherein the snap fit-type connection comprises a detent.

11. The hub assembly of claim 10, wherein the second component is configured to disengage from the first component in response to actuation of a release mechanism.

12. The hub assembly claim of 11, wherein the first component comprises a first elongate member configured to be percutaneously inserted into a patient and the second component comprises a second elongate member configured to be at least partially disposed within the first elongate member.

13. The hub assembly of claim 12, wherein the valve is configured to restrict fluid movement from the first lumen across the valve.

14. The hub assembly of claim 9, wherein the first component comprises an external ridge;
   wherein the second component comprises an external catch;
   wherein the external catch engages with the external ridge when the second component is coupled to the first component.

15. A method of accessing body tissue and/or body fluid via an introducer sheath, the method comprising:
   inserting an introducer sheath percutaneously into a patient, the introducer sheath comprising a first elongate member and an introducer sheath hub disposed adjacent a proximal end of the first elongate member, wherein a lumen extends through the first elongate member and a valve is disposed adjacent to the lumen, and wherein a portion of the valve is external to the introducer sheath hub; and
   placing a second elongate member relative to the first elongate member, the second elongate member comprising a portion that traverses the valve during placement of the second elongate member and a second elongate member hub disposed adjacent to a proximal end of the second elongate member;

wherein the valve impedes fluid movement from the lumen of the first elongate member across the valve;

wherein a portion of the lumen distal of the valve is configured to frictionally engage a protrusion of the second elongate member;

wherein the protrusion is disposed within the second elongate member hub;

wherein the introducer sheath hub comprises an external ridge;

wherein the second elongate member hub comprises an external catch;

wherein the external catch engages with the external ridge when the second elongate member hub is coupled to the introducer sheath hub.

16. The method of claim 15, wherein inserting the introducer sheath percutaneously into a patient comprises inserting the introducer sheath such that the introducer sheath does not extend within and along a longitudinal length of a vascular lumen; and the first elongate member of the introducer sheath comprises a rigid hypotube.

17. The method of claim 15, wherein a trocar is coupled to and disposed within the introducer sheath prior to inserting the introducer sheath into the patient.

18. The method of claim 17, further comprising uncoupling the trocar from the introducer sheath.

19. The method of claim 18, wherein uncoupling the trocar from the introducer does not comprise rotating the trocar relative to the introducer sheath.

20. The method of claim 18, wherein uncoupling the trocar from the introducer sheath comprises depressing a depressible button.

21. The method of claim 18, wherein uncoupling the trocar from the introducer sheath is performed with one hand.

22. The method of claim 15, wherein the portion of the lumen distal of the valve comprises a smooth taper, tapering inwardly from a proximal portion of the lumen having a larger diameter than a distal portion diameter of the lumen;

wherein the protrusion comprises a smooth taper, tapering inwardly from a proximal portion of the protrusion having a larger diameter than a distal end diameter of the protrusion; and wherein the smooth taper of the lumen distal of the valve and the smooth taper of the protrusion frictionally engage each other when the introducer sheath hub is coupled to the second elongate member hub.

* * * * *